(12) United States Patent
Xu et al.

(10) Patent No.: US 11,432,718 B2
(45) Date of Patent: Sep. 6, 2022

(54) SMART PHONE BASED VIRTUAL VISUAL CHARTS FOR MEASURING VISUAL ACUITY

(71) Applicant: EyeQue Inc., Newark, CA (US)

(72) Inventors: Ying Xu, Newark, CA (US); Yue Wang, Newark, CA (US); John Serri, Newark, CA (US)

(73) Assignee: EyeQue Inc., Newark, CA (US)

( * ) Notice: Subject to any disclaimer, the term of this patent is extended or adjusted under 35 U.S.C. 154(b) by 147 days.

(21) Appl. No.: 16/176,631

(22) Filed: Oct. 31, 2018

(65) Prior Publication Data

US 2019/0125179 A1    May 2, 2019

Related U.S. Application Data

(60) Provisional application No. 62/579,558, filed on Oct. 31, 2017.

(51) Int. Cl.
| | |
|---|---|
| *A61B 3/028* | (2006.01) |
| *A61B 3/18* | (2006.01) |
| *A61B 3/103* | (2006.01) |

(52) U.S. Cl.
CPC ............ *A61B 3/0285* (2013.01); *A61B 3/103* (2013.01); *A61B 3/18* (2013.01)

(58) Field of Classification Search
CPC ......... A61B 3/0285; A61B 3/18; A61B 3/103; A61B 3/028; A61B 3/032

USPC ....... 351/200, 222, 236, 246, 205, 223, 239, 351/237
See application file for complete search history.

(56) References Cited

U.S. PATENT DOCUMENTS

| | | | | |
|---|---|---|---|---|
| 4,571,038 | A | * | 2/1986 | Jako ..................... G02B 21/025 359/376 |
| 2018/0103841 | A1 | * | 4/2018 | Sprowl .................... A61B 3/14 |
| 2018/0196265 | A1 | * | 7/2018 | Bouchier ................ G02F 1/163 |
| 2018/0261146 | A1 | * | 9/2018 | Van 'T Hooft ....... G01R 33/283 |
| 2018/0263488 | A1 | * | 9/2018 | Pamplona ............ A61B 3/0008 |

* cited by examiner

*Primary Examiner* — Marin Pichler
*Assistant Examiner* — Alberto J Betancourt
(74) *Attorney, Agent, or Firm* — Steven A. Nielsen; www.NielsenPatents.com

(57) ABSTRACT

A system for replicating a standardized visual acuity test, such as the 20' Snellen test may comprise a binocular viewer attached to a smartphone. A binocular viewer may comprise a housing comprising a pair tube covers having voids allowing for viewing through a pair of lens tubes with each lens tube in visual communication with a second lens a first lens an aperture and a front cover. The optical systems use an artful combination of front and back lens surfaces, demagnification and other systems to faithfully replicate the sight lines perceived by a user of a traditional 20' test. The system also allows for the incorporation of other tests conducted with both eyes including Color Sensitivity and Contrast, furthermore by placing a deformable, tunable lens between the second lens and the eye the device serves as an ophthalmic refractometer, allowing a Spherical Equivalent refraction estimate for each eye.

4 Claims, 21 Drawing Sheets

Typical distance vision test performed at 20 feet away

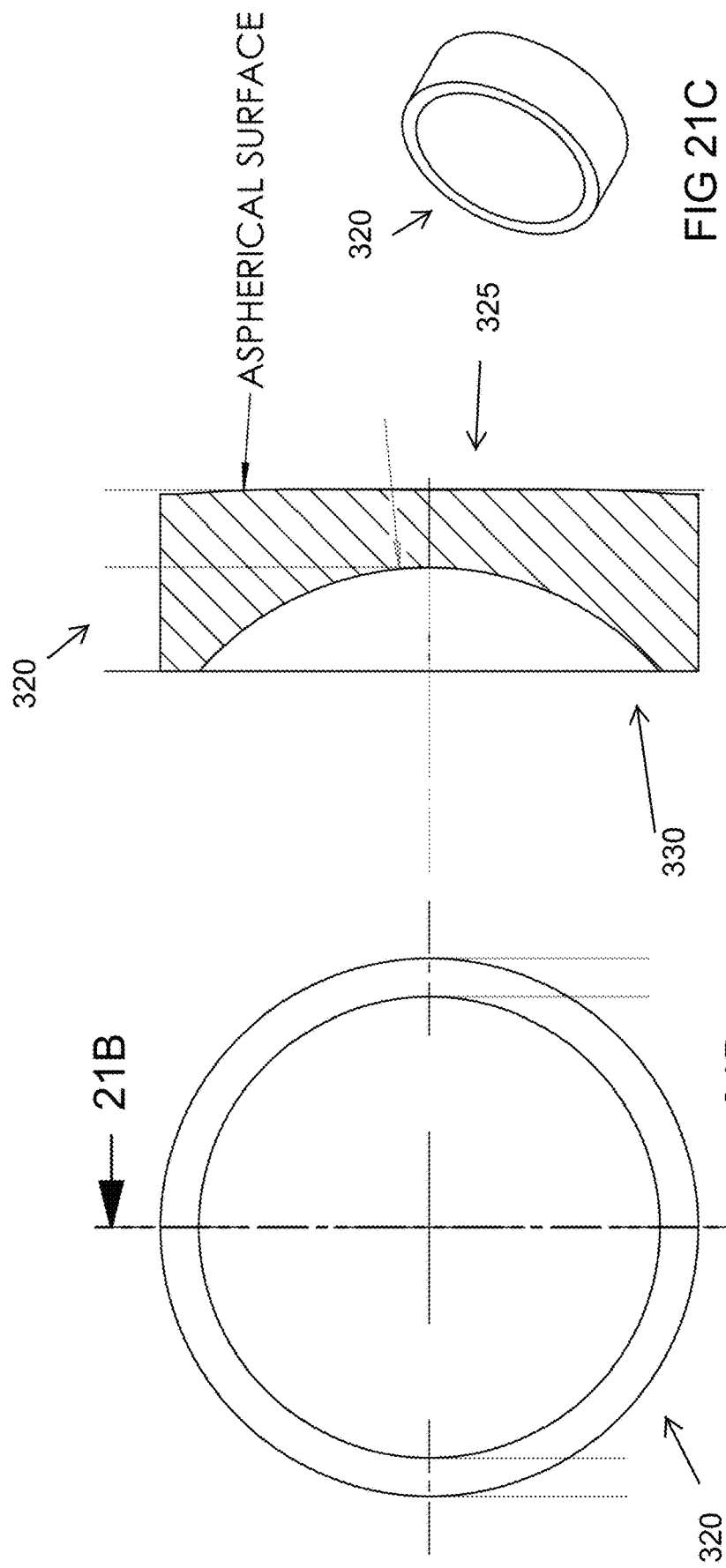

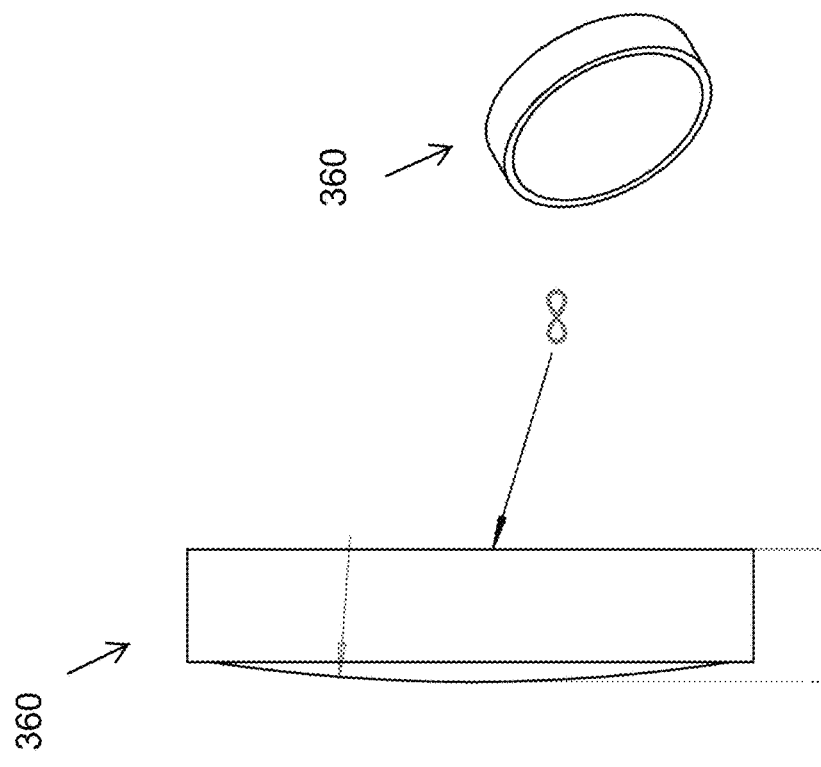
FIG. 22C
FIG. 22B
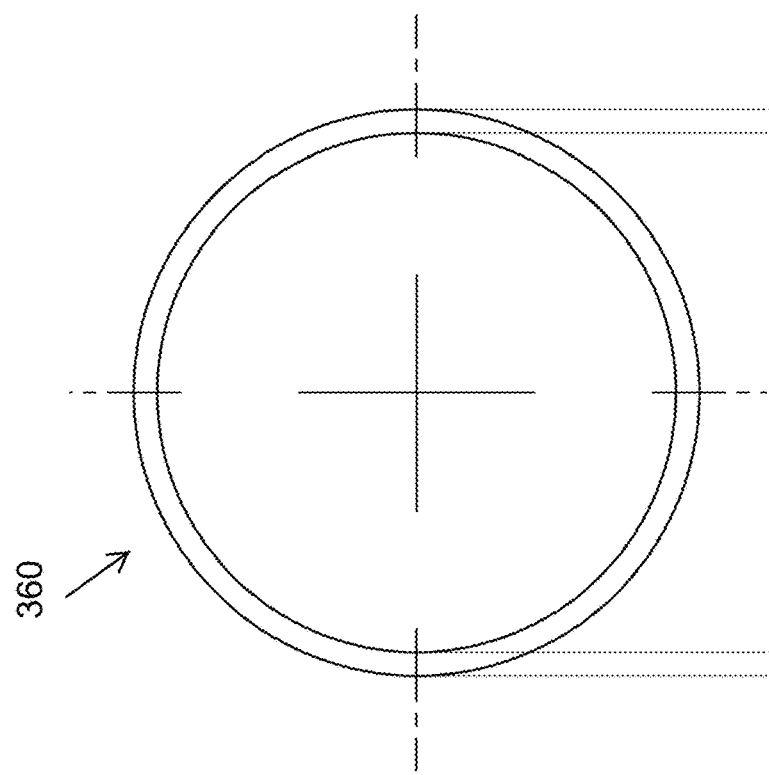
FIG. 22A

SMART PHONE BASED VIRTUAL VISUAL CHARTS FOR MEASURING VISUAL ACUITY

RELATED PATENT APPLICATION AND INCORPORATION BY REFERENCE

This is a utility application based upon U.S. patent application Ser. No. 62/579,558 filed on Oct. 31, 2017. This related application is incorporated herein by reference and made a part of this application. If any conflict arises between the disclosure of the invention in this utility application and that in the related provisional application, the disclosure in this utility application shall govern. Moreover, the inventor(s) incorporate herein by reference any and all patents, patent applications, and other documents hard copy or electronic, cited or referred to in this application.

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever. Trademarks may include "VA101" and "Visual Acuity Tracker" "Visual Acuity Screener", "Insight" and/or "EyeQue Insight".

BACKGROUND OF THE INVENTION

(1) Field of the Invention

The invention generally relates to visual acuity measurement systems. More particularly, the invention relates to the use of lens systems and nearby to user light sources to optically replicate a standard visual acuity test within the confines of a binocular viewer. Disclosed embodiments include the integration of high resolution smartphones, communication systems, data retrieval systems and other components.

(2) Description of the Related Art

In the related art, standardized visual acuity tests are well known and typically require a 20-foot distance between the test subject and the eye chart. Such tests work well in dedicated testing spaces, such as an eye doctor's office or a government motor vehicle facility. With the advent of smart phones and other electronic devices, and spending less time outdoors, children are developing myopia at an alarming rate. A shortfall in the prior art is that a parent, teacher or caregiver may want to quickly and economically test a child's visual acuity but have neither the oversized paper eyechart of the prior art nor a clear, properly lit 20-foot space. Moreover, children are not likely to stand still to maintain the required 20-foot distance of a traditional test.

The prior art is replete with shortfalls to the visual health and testing of adults as well. With the high cost of eye exams and the current need to physically travel to an eye care professional, many adults are not getting the eye tests they need. Myopia is an increasing problem and is especially acute in low income populations and worse in low-to-middle income countries.

The prior art does include the use of virtual images for eye tests, one such system is sometimes known as the SPOT Vision Screener by Welch Allyn. The Welch Allyn device is exceptionally expensive and not well suited for use by consumers. The Welch Allyn device fails to leverage the high-resolution screens of present day smart phones. The Welch Allyn device requires a three-foot distance between the device and the test subject, making the device unsuited for self-testing. Thus, there is a serious short fall in the related art and room in the art for the presently disclosed embodiments.

Recently, there has been a plethora of free mobile Apps that claim to measure visual acuity, but in order to duplicate the 20' Snellen test, the phone screen needs to be far away from the user, making the testing highly inconvenient, and in the case of testing children almost impossible. Also, given the fact that there is no constraint on the distance of the tester from the smart phone in these free Apps the results are highly inaccurate, compared to the forced distant constraints of the presently disclosed embodiments.

BRIEF SUMMARY OF THE INVENTION

The present invention overcomes shortfalls in the related art by presenting an unobvious and unique combination, configuration of disclosed components that include two sets of lenses with optical properties well suited for optically producing a traditional visual acuity test within the relatively short confines of a binocular viewer. The term "visual acuity" may be defined as the eye's ability to detect fine details at a predefined distance. Disclosed embodiments overcome shortfalls in the art by the artful use and integration of high resolution smart phone screens that a provide finely tuned light source. The integration of high resolution smart phone screens also provides infinite possibilities in the presentation of eye charts or symbols used for eye testing. Moreover, the integration of smartphones facilitates the instant analysis of test results and instant communication and electronic storage of test results.

The present invention provides a self-administered vision test solution, which yields similar results as the prior art vision test performed in a doctor's office. With a disclosed binocular viewer working in conjunction with a smartphone running a specific application, the user can perform a self-administered distance (or near) vision test without additional help. Furthermore the system, comprised of the binocular viewer and the smart phone can also be used to conduct other visual tests including contrast sensitivity, color sensitivity, and refractive error. The present invention also provides a method for a user to manage their eye health by providing referrals to eye care professionals. The invention also provides a means for electronic communication between a user, and/or an eye care professional.

The disclosed embodiments overcome shortfalls in the prior art by the use of demagnification occurring on the back side of the first lens which comprises a concave surface.

The disclosed embodiments overcome shortfalls in the art by providing an economical, compact and self-administered visual acuity test that comports with the limited means of many people. The traditional field test often conducted at 20 feet (or 6 meters) to replicate real life visual needs wherein objects 20 feet away are of real relevance. A person of "normal" vision may be said to have 20/20 vision, meaning that the test subject sees the 20/20 line of optotypes (letters, numbers, tumbling E, etc.) at a 20 foot distance. A test subject with "better than normal" vision will see the 20/15 line of optotypes (smaller size than 20/20 line) at a 20-foot distance, deeming them capable of 20/15 vision. Conversely, a test subject with significantly "less than normal" vision such as 20/200 has vision that is 1/10th that of a person with normal vision or would need the objects 10 times closer to see the same 20/20 line that a person with normal vision sees at 20 ft. Based upon the real world need to see objects at 20 feet with clarity, many visual acuity standards are based on the 20 foot bench mark. Thus, virtually replicating the 20 foot bench mark test is of great utility, so long as such virtual or optical replication tests the viewer's ability to resolve an object subtending at an angular range of 20 feet. The presently disclosed embodiments not only simulate the angular view lines of a 20 foot test, but also improve upon the traditional 20 foot test by use of randomly rotating optotypes, static lighting, immediate test result reporting, test analysis and electronic storage.

Moreover, replicating the standard 20 foot test is of utility in detecting a number of conditions including refraction error, astigmatism, myopia, hyperopia, color blindness, glaucoma, and macular degeneration for example.

By inserting an adjustable lens system between lens (360) and the user, the device also serves as a portable phoropter. The user adjusts the power of the lens to reach best visual acuity. As the light emerging from lens (360) representing the screen is nearly parallel, adjusting the lens system will serve to focus the light on the retina.

Accurate refraction values can be achieved by using an adjustable stokes cylindrical lens pair and adjustable spherical lens to offset astigmatic as well as spherical errors for the tunable lens system. Refractive values are used in determining the refraction correction supplied by devices such as prescription eye glasses.

In particular, myopia is the medical term for the common vision condition known as nearsightedness, in which close vision is sharp, but objects farther away appear blurred. The prevalence of myopia has rapidly increased globally over the last 30 years. There is a substantial risk for vision impairment associated with high myopia, including retinal damage, cataract and glaucoma. Myopia is estimated to affect 27% (1.9 billion) of the world population, in 2010. Myopia is projected to effect 33% (2.6 billion) of the world population by 2020 and 50% (5 billion) of the world's population by 2050, according to a World Health Organization (WHO) myopia report.

The disclosed embodiments are well suited for testing the vision of children as the disclosed binocular viewer may be used in small rooms or crowded conditions where securing an eye chart at exactly 20 feet from a test subject and proper lighting is not practical.

Vision problems currently affect 1 in 4 school-aged children in the US and the ratios are even higher in other countries such as Korea and China. Impaired vision in children can cause life-long learning, emotional and behavioral problems. The American Optometric Association recommends a comprehensive eye exam every one to two years. However, due to the rapid development of a child's eye balls, myopic conditions given this timeframe may not be detected until after they have been progressed to a significant degree. Research studies prove that the progression of myopia in children can be slowed or stopped, resulting in better vision for life. Early detection and intervention is paramount in slowing myopia progression in school-aged children. Thus, the presently disclosed embodiments are necessary in providing a convenient, low cost self-administered and easily accessible methods to monitor vision changes, such as the onset of myopia. The disclosed embodiments have global utility. In under-developed countries, there is a dearth of eye care professionals, making vision screenings unavailable to many. Thus, the disclosed embodiments are crucial in providing, access to self-administered and easy-accessed vision screening tools to test visual acuity as a first step towards treatment.

Currently, distance vision tests are normally performed at a doctor's office, as the first step of the comprehensive eye exam to assess visual acuity. In the prior art, the test subject typically stands at a significant distance, usually 20 ft (or 6 meters), from the visual target. The visual target contains different letters with various sizes (Snellen chart), or different orientations of the letter "E" with varies sizes (tumbling E chart) or different orientations of the letter "C" with various sizes (Landolt C chart). The examiner asks the test subject to identify the letters or the orientations of the letters corresponding to a given line on the chart, with each descending chart line comprising letters of smaller size.

The invention comprises a method for self-administered vision screening, which includes the steps of requesting user information, performing visual acuity tests at distance or near, reporting visual acuity results, and tracking visual acuity changes. The results are instantaneously shown on the smartphone after the test, and are stored on a secured cloud server.

A smartphone is used as a display, to create the visual target. In one embodiment, the visual target is chosen to be the tumbling E chart, where the letter "E" with random orientations including up, down, left and right is displayed. The smartphone is attached to the optical device, in a similar fashion as a smartphone is attached to a virtual reality headset. The optical device comprises a unique lens system, which projects the E chart displayed on the smartphone to a virtual distance of 20 feet (6 meters) for distance vision and 14 inches (35 centimeters) for near vision.

The smartphone generates a visual target with white background and black letters, in a similar appearance as a traditional physical eye chart. However, unlike a printed, static and predictable tumbling E chart of the prior art test, in the present embodiments, the letter E and its orientation is randomly generated by the smartphone during the test. Thus, the sequence of letter E orientations is different for each test, minimizing the memory effect which may skew test results.

In one contemplated method of use, a user looks through the binocular viewer with the smartphone attached and uses finger swiping on the touchscreen of the smartphone to interact with an IOS or Android application. Using the swiping gestures of up, down, left and right, the smartphone application receives user input based on the user's perceived current E orientation displayed on the smartphone. After the test, the smartphone application calculates the visual acuity values and displays the results on the screen. A vision record is created and stored upon a secured cloud server, with a time stamp. Over time, a history of vision tests is created and can be used as a reference for monitoring vision changes.

For users who are already moderately myopic or hyperopic, measuring visual acuity without correction would not be appropriate to measure the efficacy of the user's current correction. Thus, disclosed embodiments allow testers to wear either contact lenses or frame glasses, to verify if their current prescription of correction lenses are appropriate, or in other words, if the correction provided by the contacts or the eyeglasses facilitates improved vision, with 20/20 vision being a benchmark.

In the disclosed database systems, the recorded history of vision test results may be shared with parents or eye care professionals, via emails or alerts, wirelessly, minimizing communication cost and time.

Disclosed embodiments include means and methods of ascertaining a test subject's pupillary distance or PD using the smartphone application.

Disclosed embodiments may measure presbyopia and/or act as a phoropter, with tunable spherical and cylindrical values.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 21A depicts a front view of a first lens FIG. 21B depicts a side view of a first lens FIG. 21C depicts perspective view of a first lens FIG. 22A depicts a front view of a second lens FIG. 22B depicts a side view of a second lens FIG. 22C depicts a perspective view of a second lens

REFERENCE NUMERALS IN THE DRAWINGS

Figure 1:
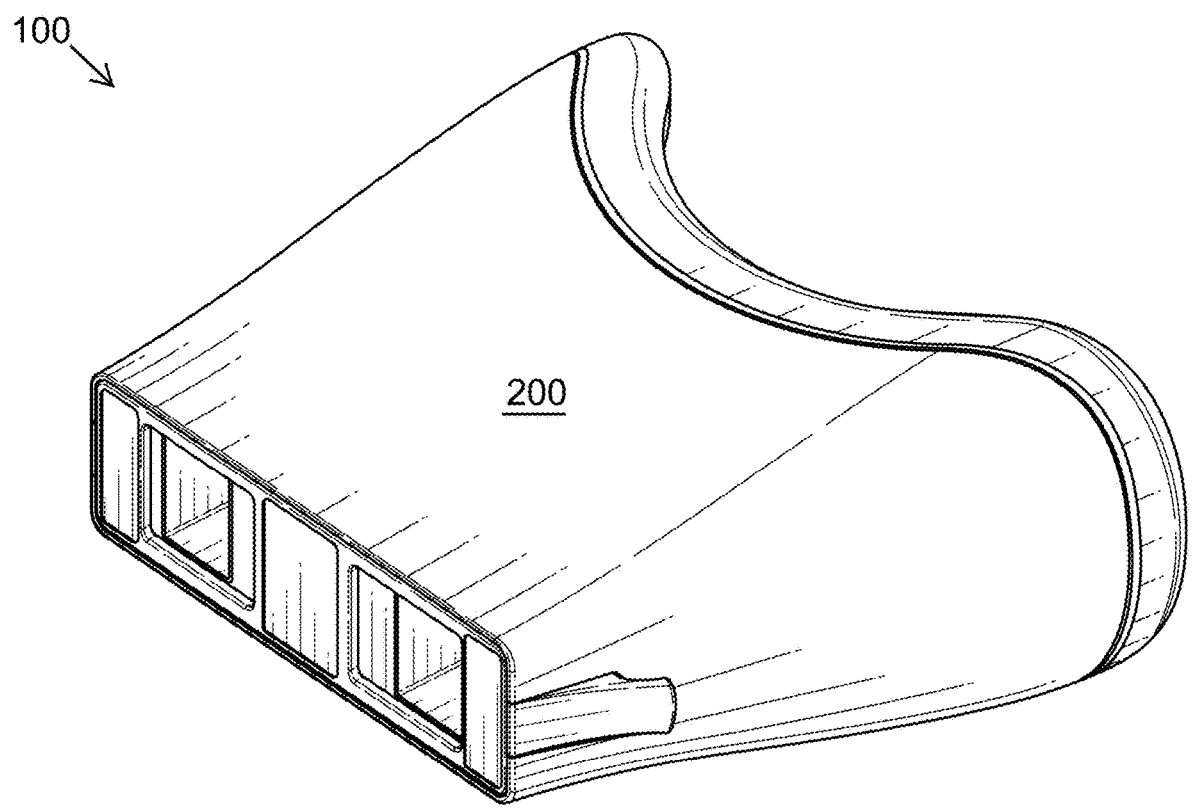
FIG. 1 depicts a front perspective view of a disclosed binocular viewer embodiment

100 a disclosed embodiment in general
200 housing
205 window
210 foam padding
220 fastener
222 face insert
225 face tube
227 pin guide
240 PD wheel
242 PD knob
245 tube cover
247 hook
250 lens tube
253 pinion gear
254 PD gearing
255 aperture
257 gear cover
260 front cover
265 micro suction tape
300 lens system in general
310 proximal or near eye point of sight rays
320 a first lens
325 first surface or front surface comprising a aspherical surface of a first lens 320
330 second surface or back surface comprising a concave surface of a first lens 320
360 a second lens or spherical convex lens
380 distal or far eye point of sight rays
400 smart phone or other personal electronic device
405 display or screen surface of smartphone
410 strap to secure smart phone to housing
500 eye chart
600 human eye
620 eye lens
640 retina
700 cloud storage/communication system
720 database of user information
740 database for eye care professional
760 database for production of eyeglasses
800 adjustable lens system for refractive correction and other functions These and other aspects of the present invention will become apparent upon reading the following detailed description in conjunction with the associated drawings.

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

FIG. 1 depicts a disclosed embodiment 100, sometimes referred to as the EyeQue Insight™, optical device or binocular viewer. In general, the disclosed embodiments provide compact, portable and economic means to replicate a standard vision test. In a standard vision test, a test subject is positioned 20 feet from a physical eye chart. Using the disclosed embodiments, the same experience and test results are replicated by use of a binocular viewer and smartphone. Unlike the prior art, the presently disclosed embodiments seamlessly integrate with electronic storage media, such as cloud systems. In general, disclosed components are encased in a housing 200.

Figure 2:
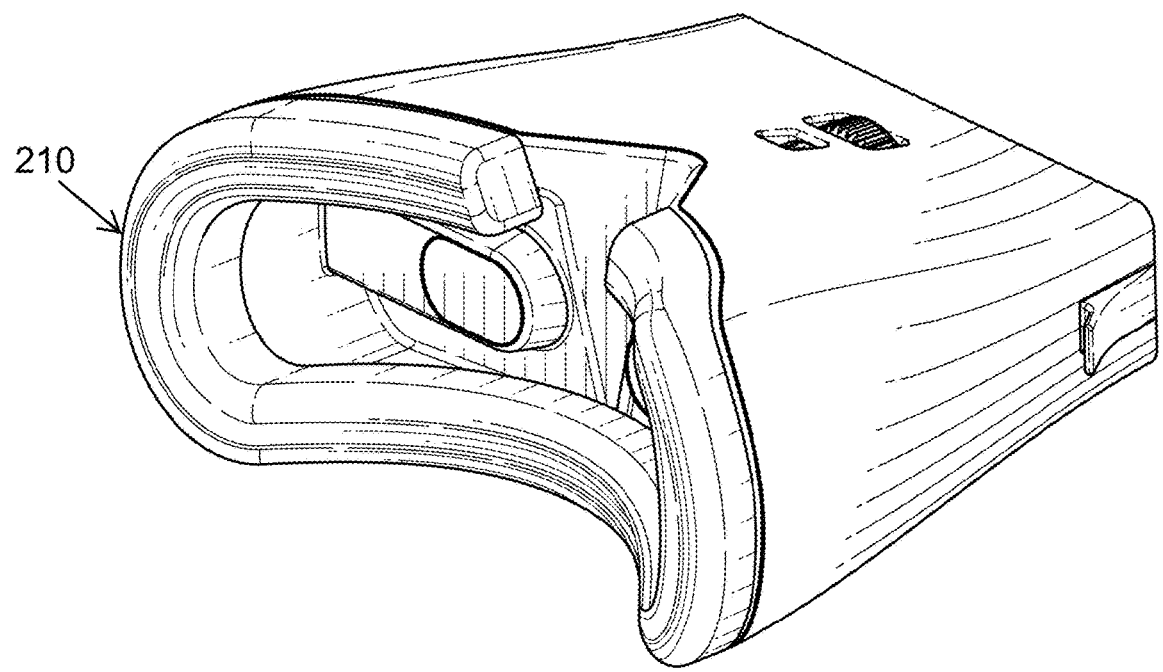
FIG. 2 depicts a rear perspective view of a disclosed embodiment

FIG. 2 depicts a perspective view showing a strip of foam padding 210 in the foreground.

Figure 3:
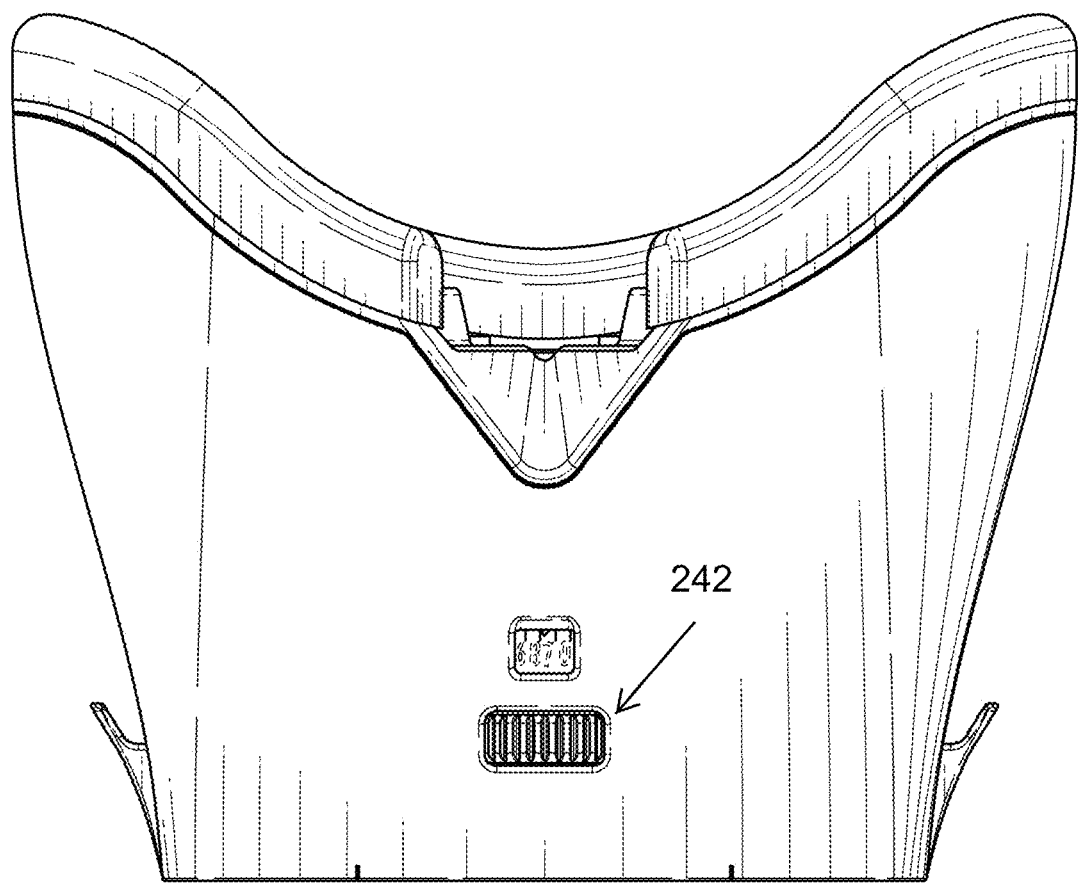
FIG. 3 depicts a top view of a disclosed embodiment

FIG. 3 depicts a top view showing a PD knob 242 used to set the user's estimated pupillary distance or PD. By viewing indicia displayed upon a smart phone, the disclosed embodiments allow a user to rotate the PD knob 242 to align the interval between the barrels to the user's PD. The measured PD is displayed upon the PD wheel 240.

Figure 4:
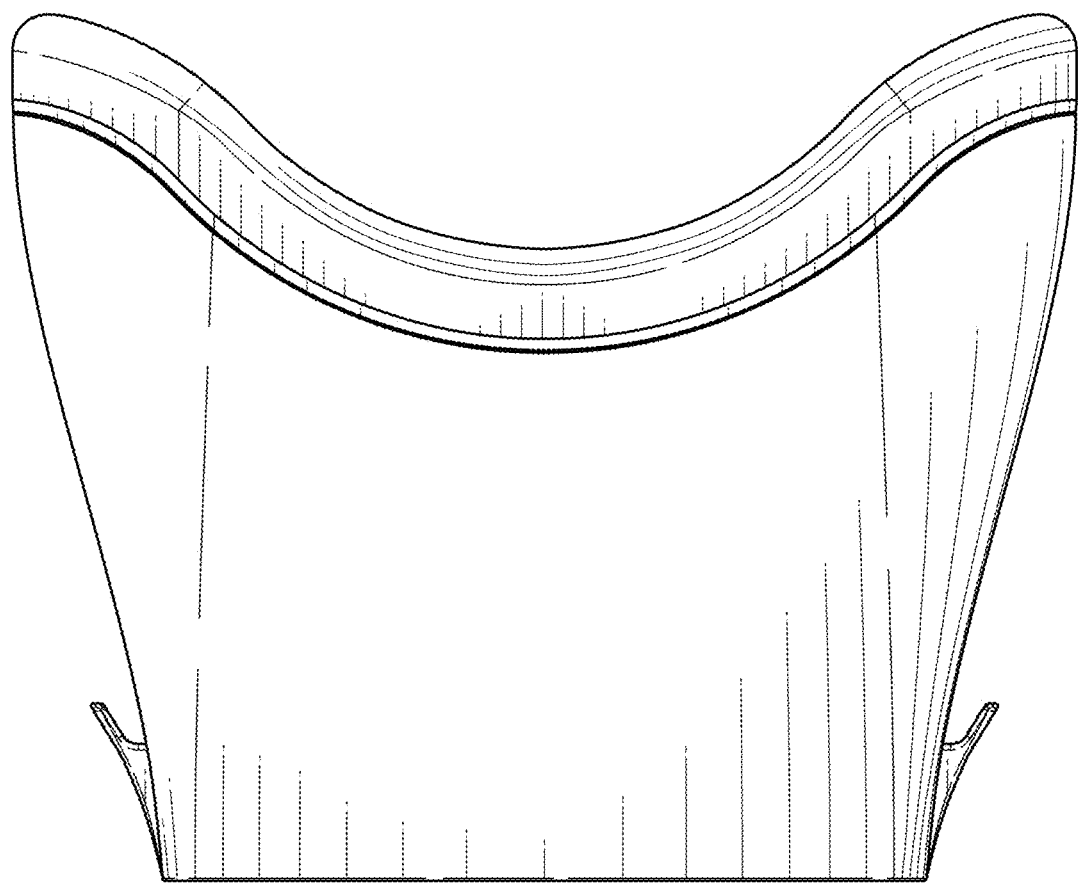
FIG. 4 depicts a bottom view of a disclosed embodiment

FIG. 4 depicts a bottom side view of a disclosed embodiment.

Figure 5:
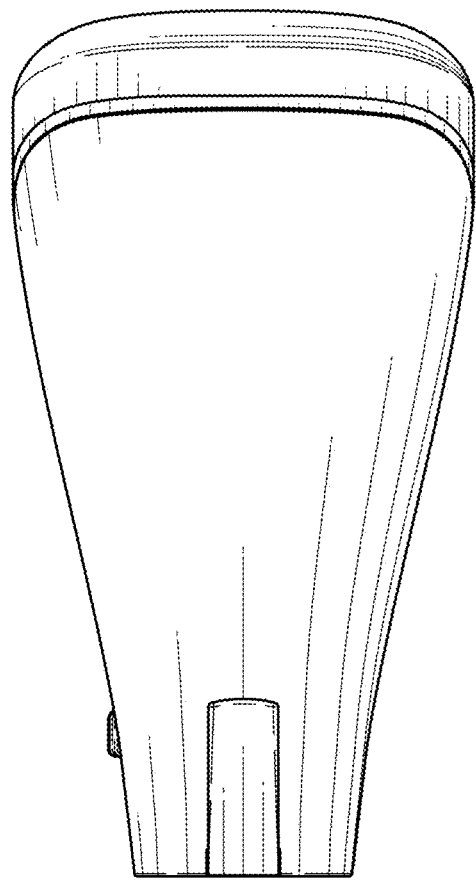
FIG. 5 depicts a left side view of a disclosed embodiment
Figure 6:
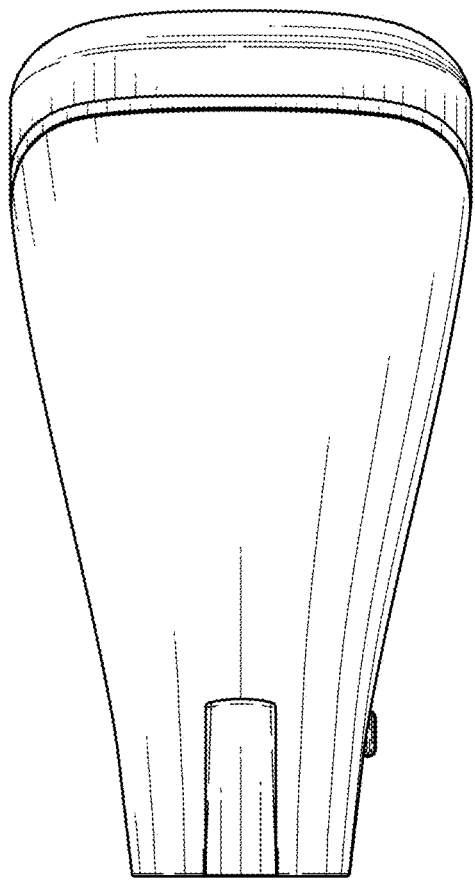
FIG. 6 depicts a right side view of a disclosed embodiment

FIG. 5 depicts a right side view and FIG. 6 depicts a left side view.

Figure 7:
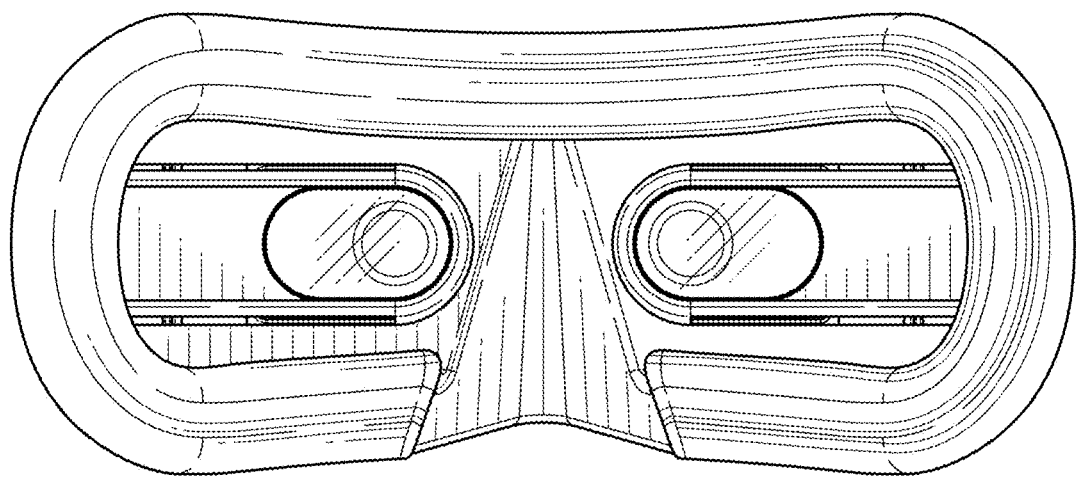
FIG. 7 depicts a rear view of a disclosed embodiment
Figure 8:
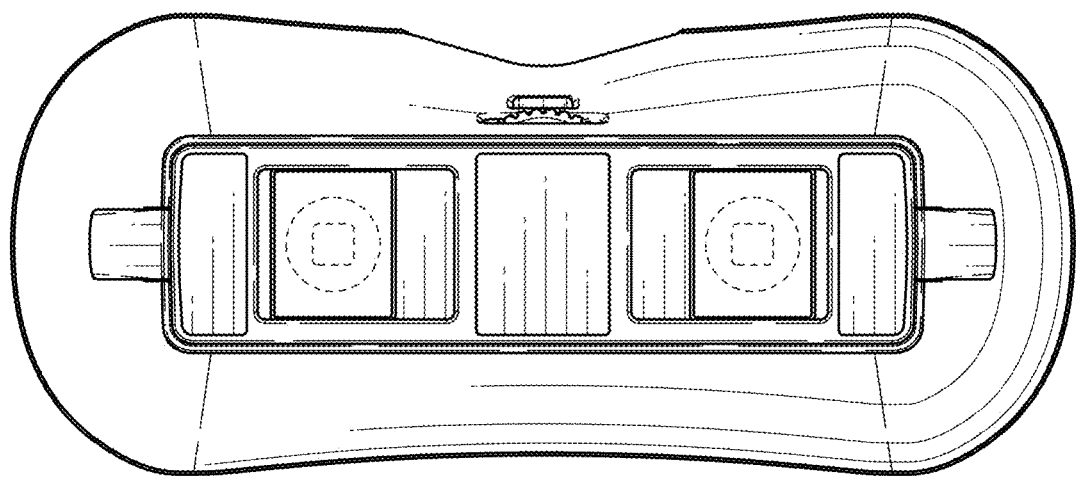
FIG. 8 depicts a front view of a disclosed embodiment

FIG. 7 depicts a front view and FIG. 8 depicts a back view.

Figure 9:
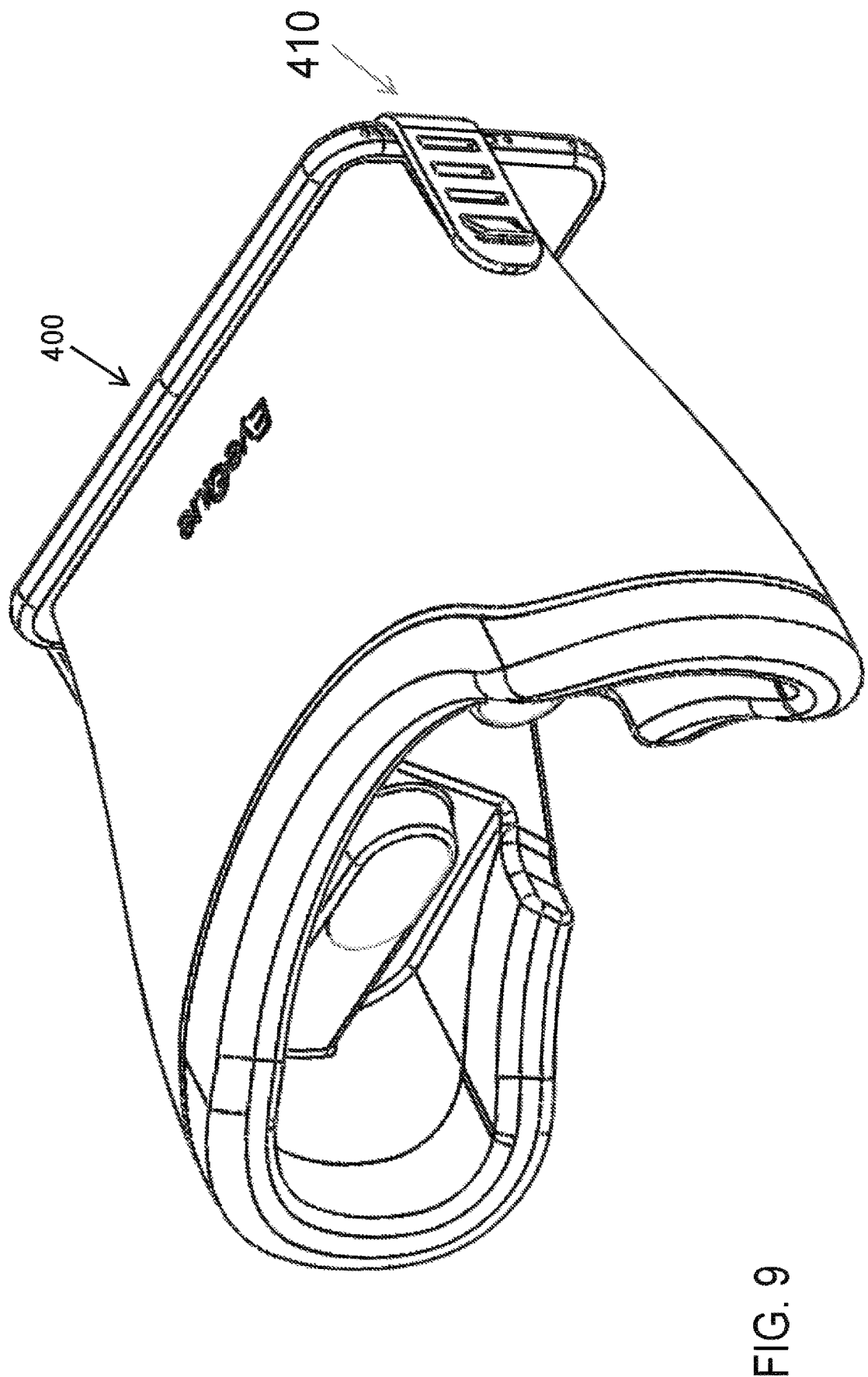
FIG. 9 depicts a rear perspective view of a disclosed embodiment with a smart phone attached

FIG. 9 depicts a front and side perspective view with a smart phone 400 or other personal electronic device attached to the back side of the device. A strap 410 or other fastener may be used to secure the phone to the housing.

Figure 10:
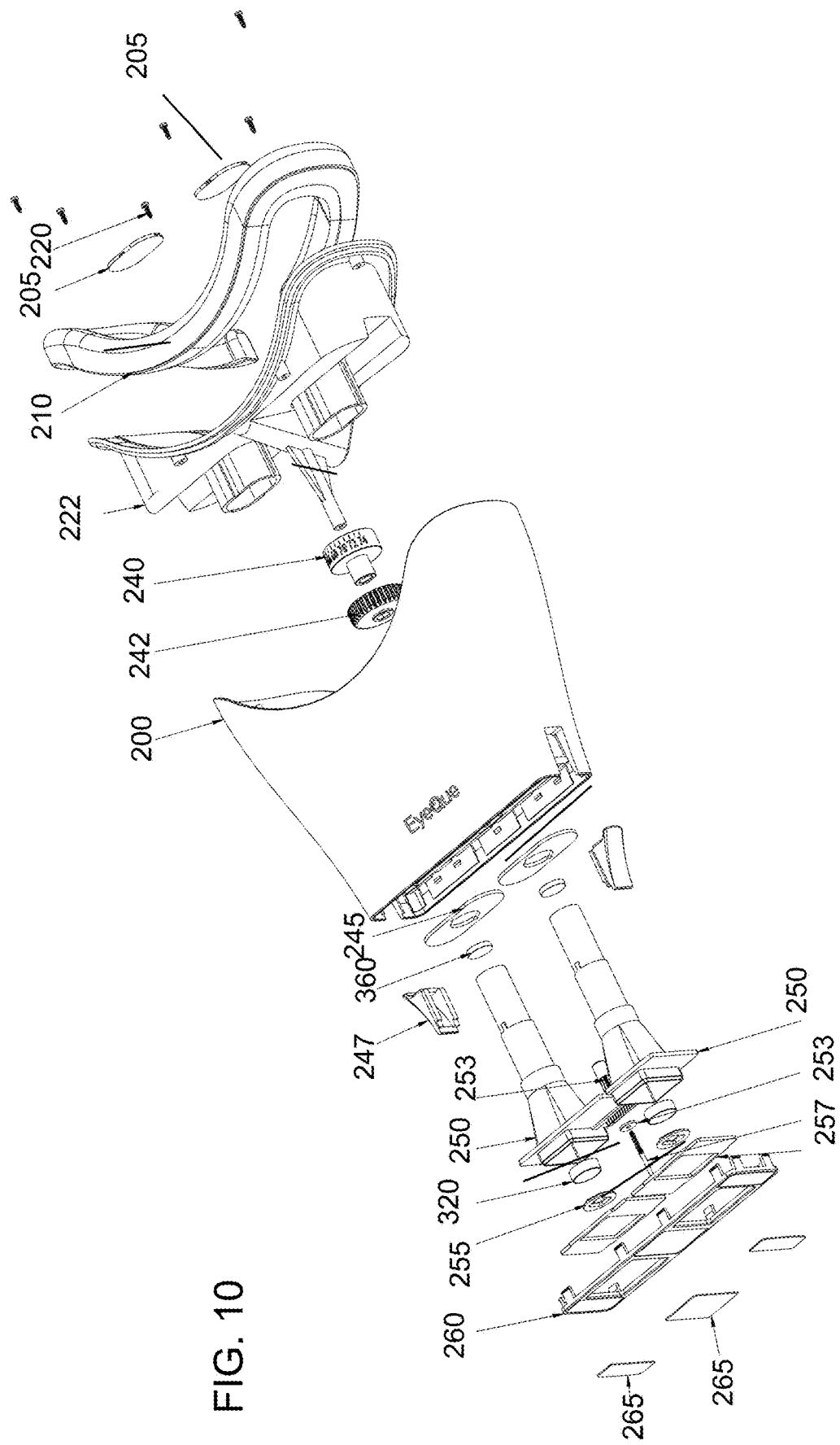
FIG. 10 depicts an exploded view of a disclosed embodiment

FIG. 10 depicts an exploded view of a disclosed embodiment which may comprise a lens system 300 comprising a first lens 320 or first set of lenses and a second lens 360 or second set of lenses. In general, the lens system optically simulates the prior art vision test requiring 20 feet of space by use of a system requiring less than 11 or so inches. The first and second sets of lenses are secured within lens tubes 250, with the lens tubes moved along the horizontal plane to comport with the user's PD or estimated PD. The user's PD is acquired by the presentation of images upon a smart phone with the distance between the tubes adjusted to the user's PD. A PD knob 242 may be adjusted by the user and the derived PD value or estimated PD value may be observed by viewing the PD wheel.

Starting from the eye of a user or in a proximal position, a window 205 may comprise a transparent flat surface which keeps debris out of the system. Fasteners 220 may attach a face insert 222 upon the housing 200. The windows 205 may be disposed upon or within the face insert and the windows may be centered or aligned to face tubes 225 with the face tubes aligning to a respective lens tube 250.

A pin guide 227 may be disposed upon the face insert 222, with the pin guide axially connected through the PD wheel 240 and PD knob 242. The exterior ends of the face tubes may be aligned within the voids defined by the tube covers 245. The voids defined by the tube covers 245 may be aligned to or may help retain the first set of lenses. The second set of lenses 360 may be retained in or aligned to the proximal ends of the lens tubes 250. The distal ends of the lens tubes may retain or be aligned with the first set of lenses 320. Aperture pieces 255 may define aperture voids with the aperture voids aligned to the first set of lenses 320. A gear cover 257 may be secured to the distal ends of the tubes and a front cover 260 may be secured over the gear cover and within or upon the housing 200. Micro suction tape 265 or other types of fasteners may be applied to the distal side of the front cover 260, with the distal side of the front cover having a planar finished surface to comport to the planar surface of a screen of a smart phone or other electronic device.

Figure 11:
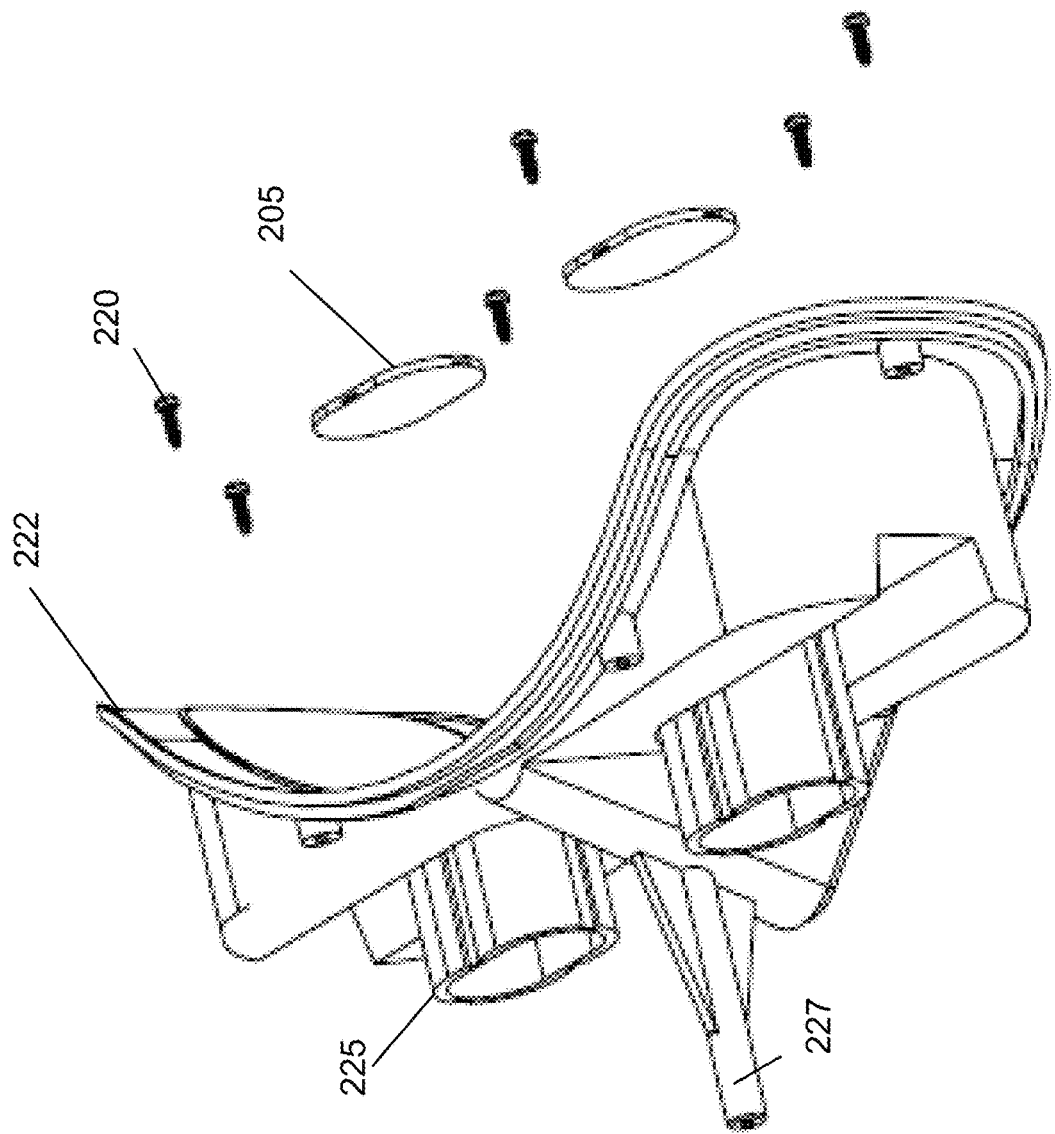
FIG. 11 depicts disclosed a face plate and other components

FIG. 11 depicts an expanded view of a face insert 222 and related components.

Figure 12:
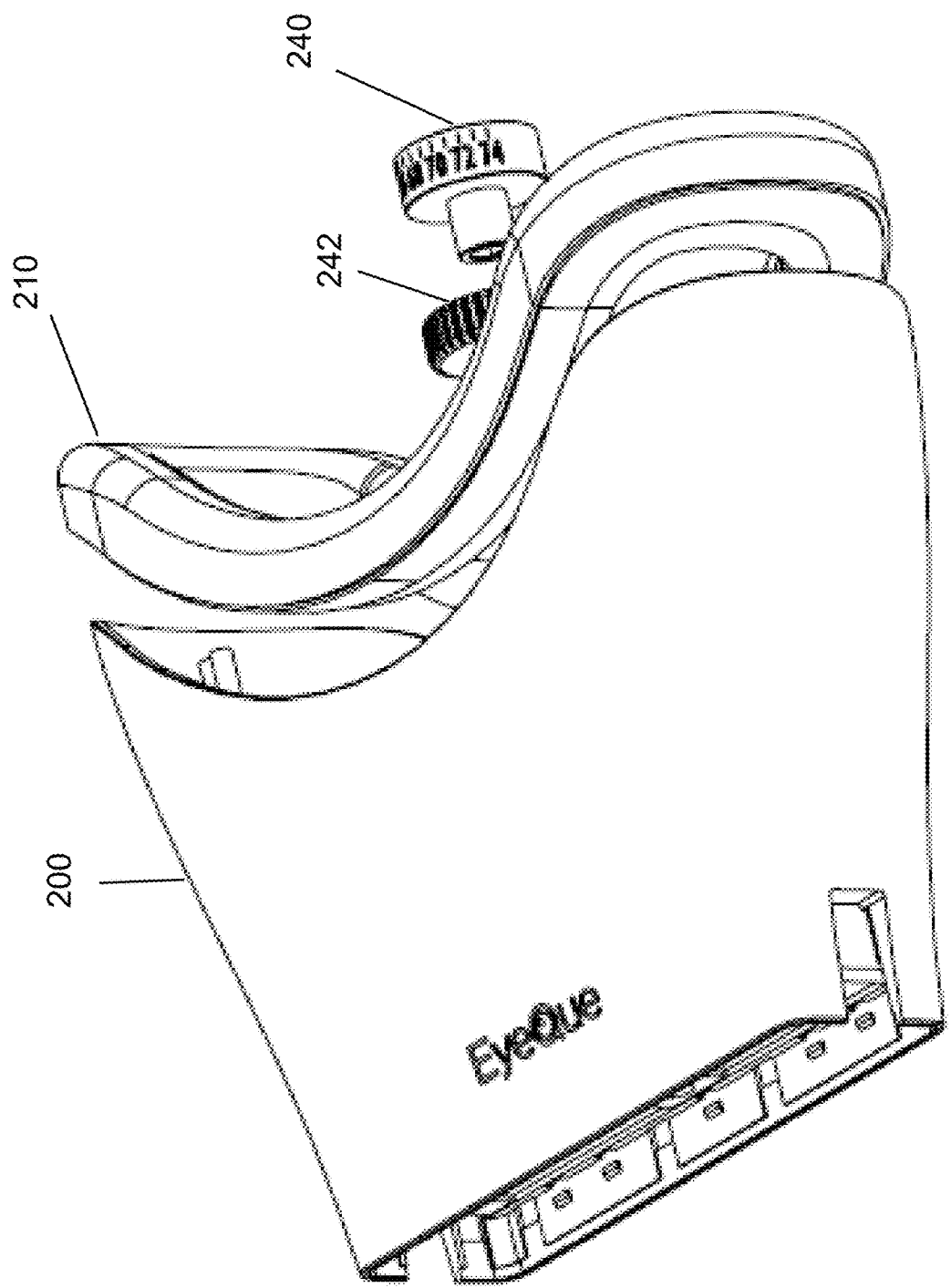
FIG. 12 depicts a disclosed housing and other components

FIG. 12 depicts an expanded view of a housing, strip of foam padding 210, PD knob 242 and PD wheel 240. The PD wheel may comprise markings or indicia indicating a PD obtained or estimated PD in reaction to user adjustments of the PD knob 242.

Figure 13:
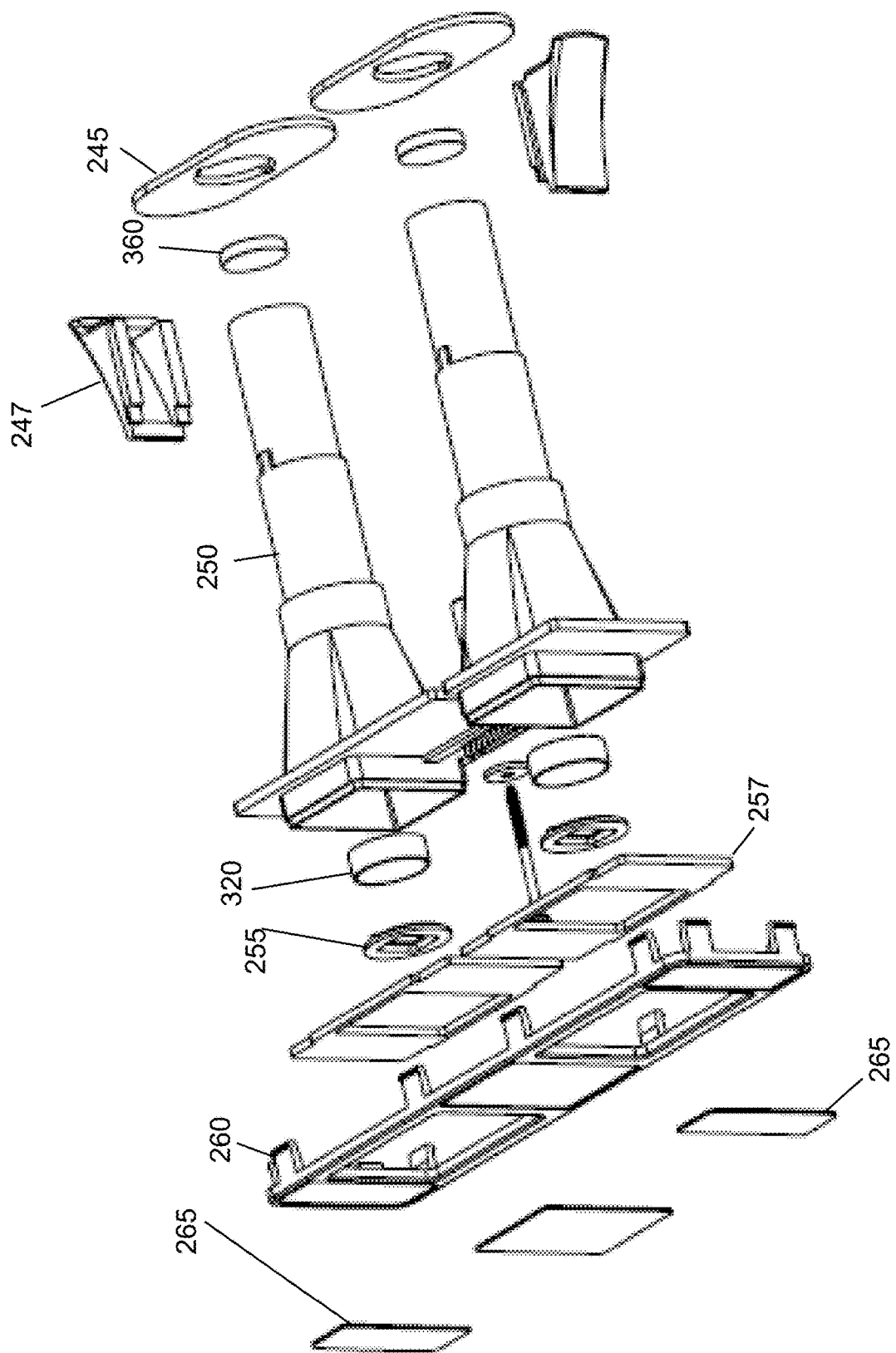
FIG. 13 depicts disclosed components disposed within the binocular viewer

FIG. 13 depicts an expanded view of the more distal components of the disclosed embodiments.

Figure 14:
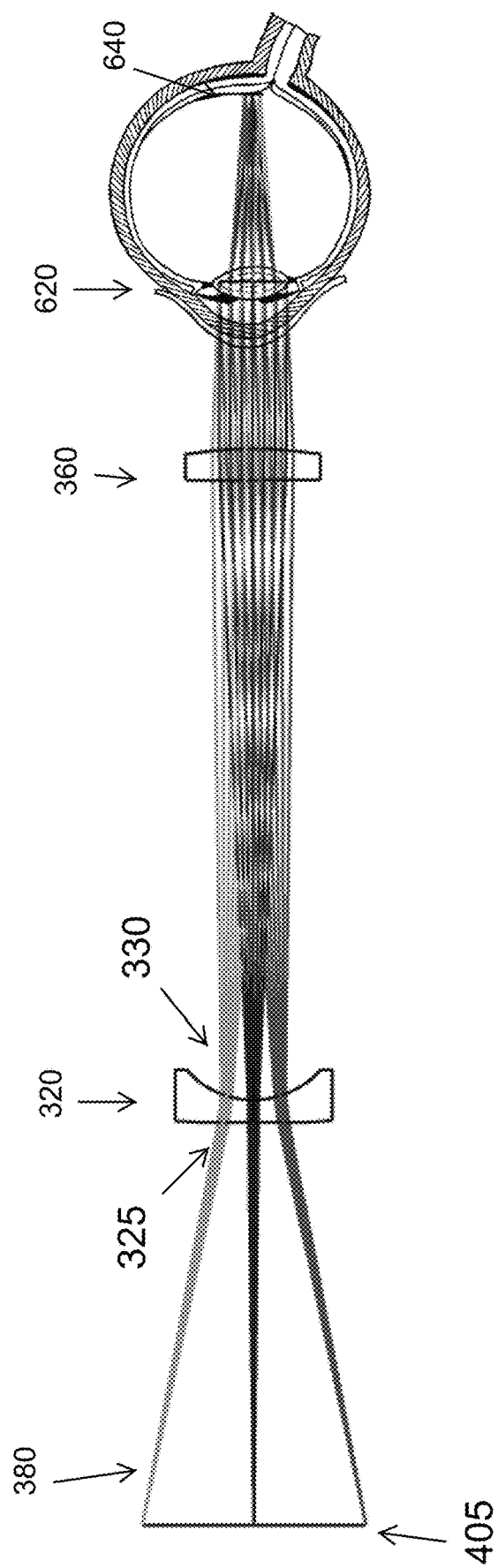
FIG. 14 depicts a tracing of vision ray lines

FIG. 14 depicts sight lines or sight rays obtained by a disclosed lens system. Sight rays may start upon or be generated by screen surface 405 of a smart phone. The sight lines or a smart phone image may enter an aspherical surface 325 of a first lens 320. Light will then enter a concave surface 330 of the first lens. Demganification occurs as a result of the first lens, enabling the production of optically presented optotypes, with the optotypes having the same sight lines as optotypes presented in physical paper form at 20 feet.

The image or light then enters a second lens 360, the second lens comprising a spherical convex lens. The image or light then enters eye lens 620 and then the retina 640.

Figure 15:
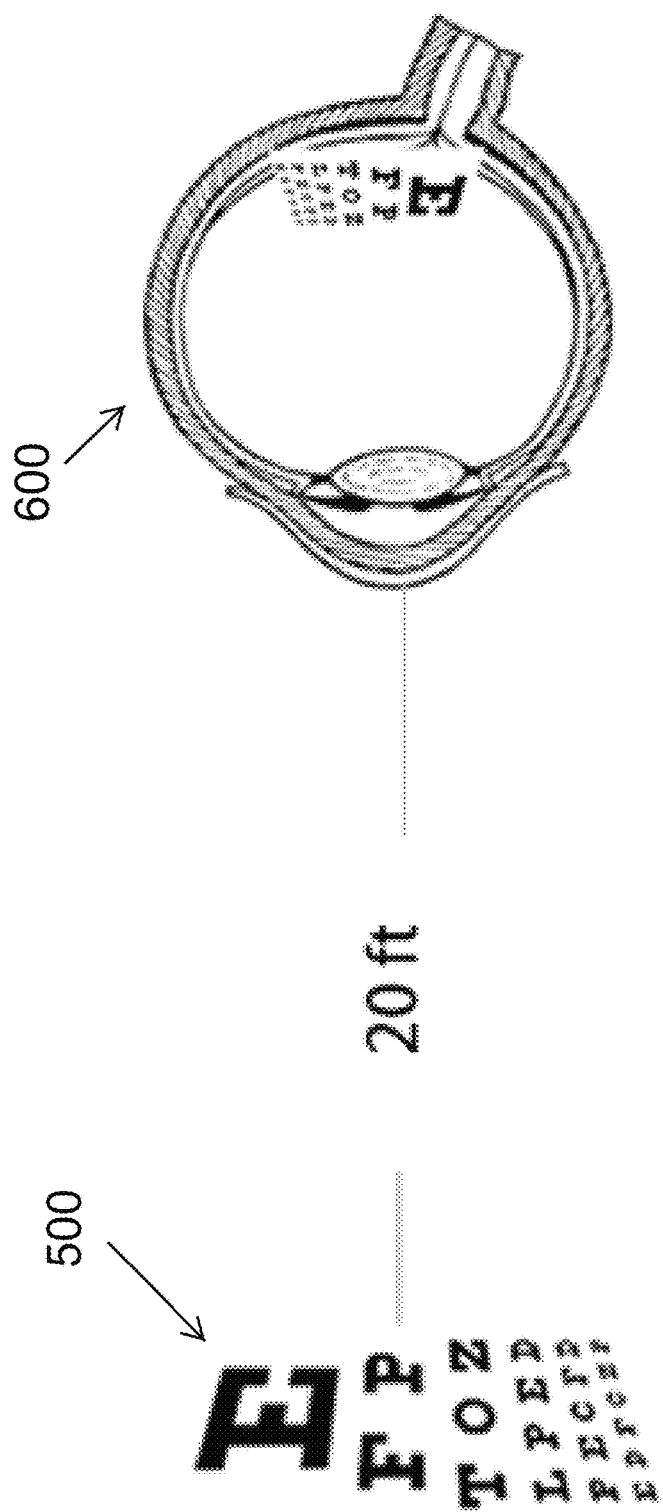
FIG. 15 depicts a typical distance test

FIG. 15 depicts a typical distance vision test wherein the subject and eye chart are at a distance of 20 feet.

Figure 16:
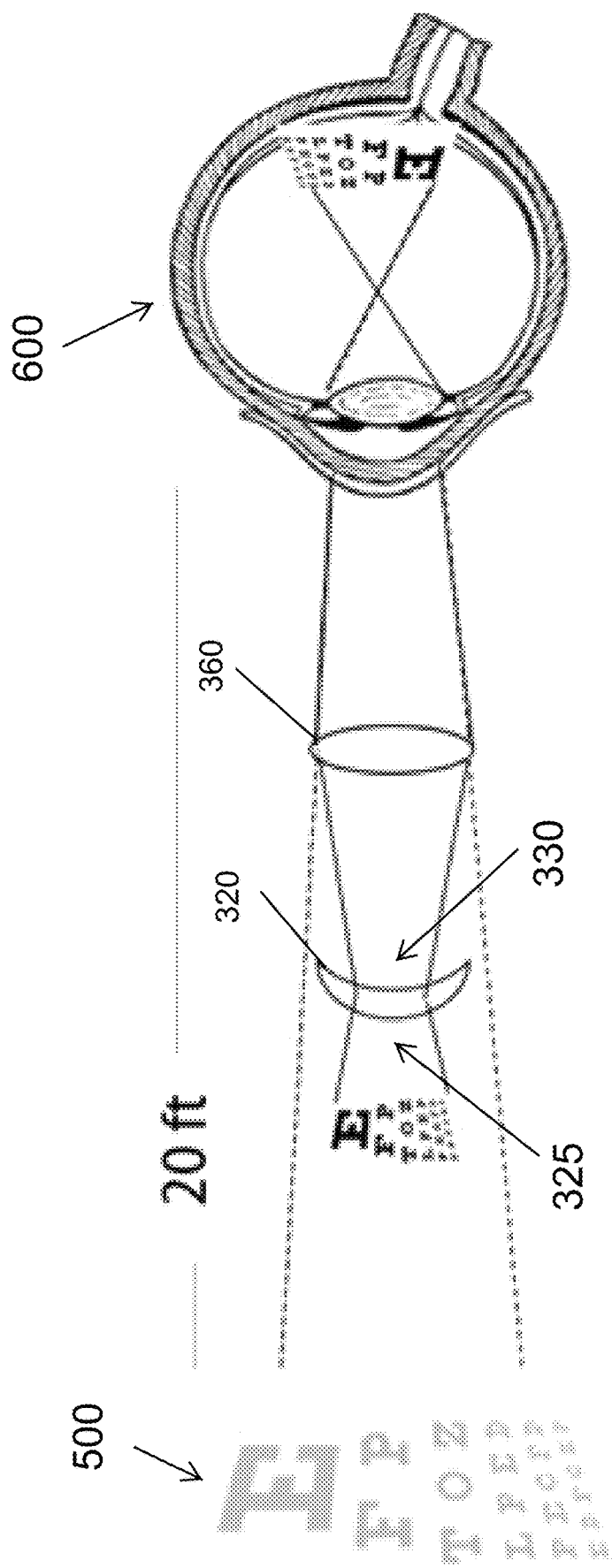
FIG. 16 depicts a disclosed testing system as compared to a traditional system

FIG. 16 depicts a comparison of the traditional eye test at 20 feet to the optics of a disclosed embodiment. The artful combination of the first 320 with the second lens 360 creates compact and portable visual acuity test system achieving the same results as the 20 foot test of the prior art. Thus, the images viewed from a disclosed embodiment have the same optical qualities of images viewed in the prior art 20 foot vision test.

Figure 17:
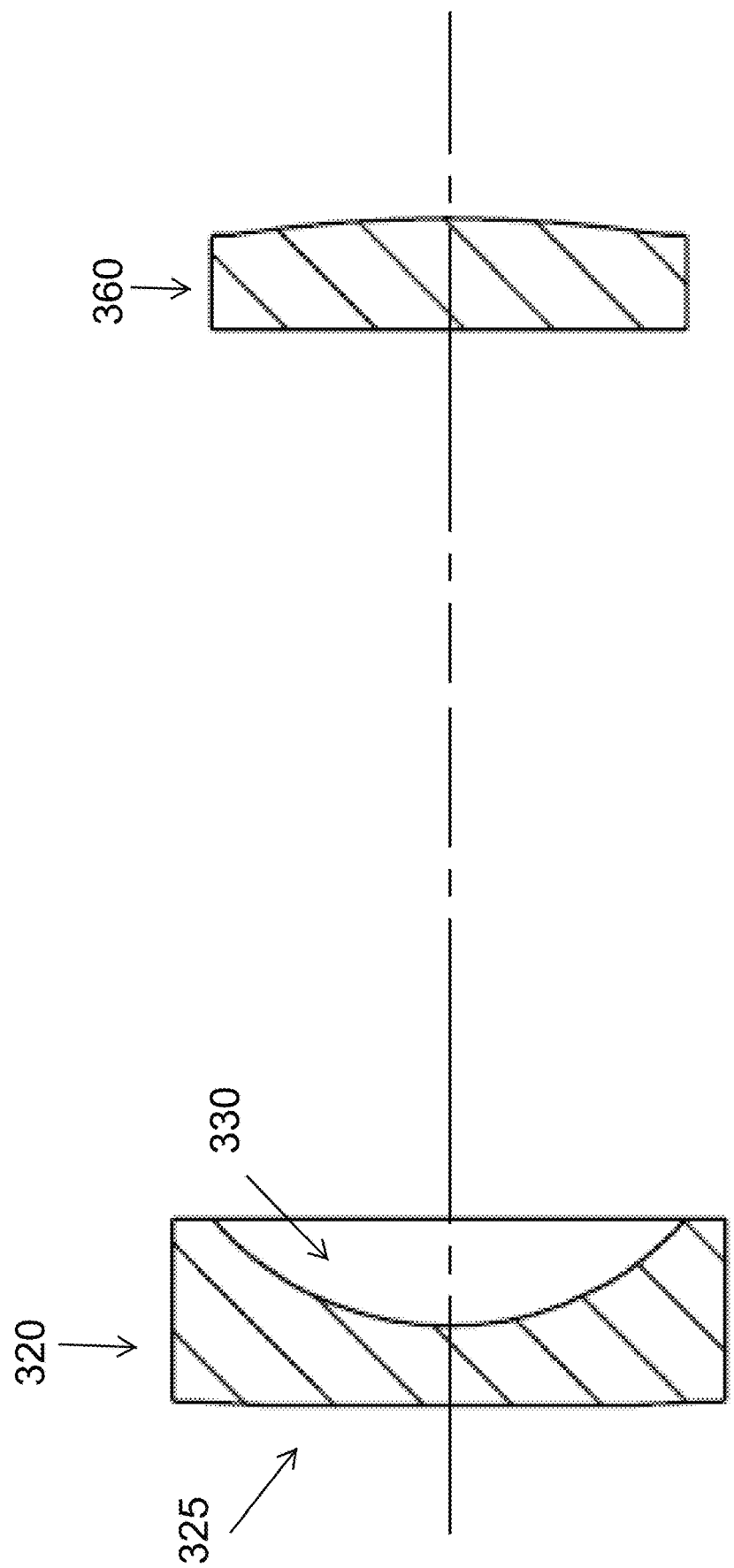
FIG. 17 depicts a sectional view of a disclosed optical system

FIG. 17 depicts a first lens 320 or lens near the smartphone screen, with the first lens having a first or front side 325 comprising an aspherical surface. The first lens 320 may have a back side comprising a concave surface. A second lens 360 may comprise a spherical convex lens.

Figure 18:
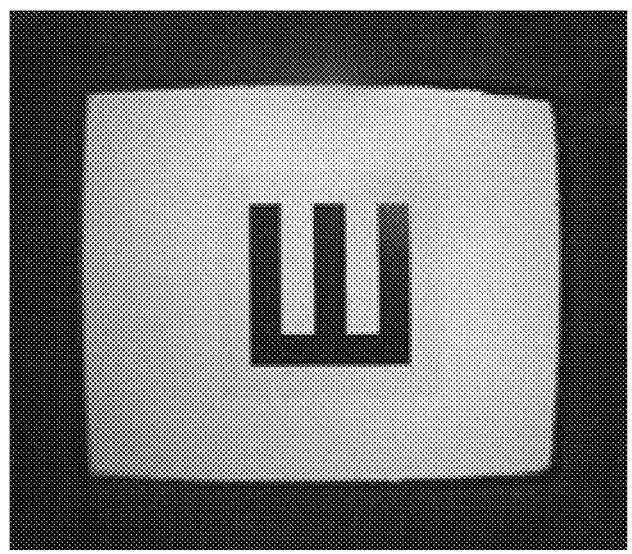
FIG. 18 depicts a blurred image of the prior art

FIG. 18 depicts a barrel distortion of the prior art. The disclosed use of the front aspherical surface of the first lens helps to reduce the barrel distortion of the prior art.

Figure 19:
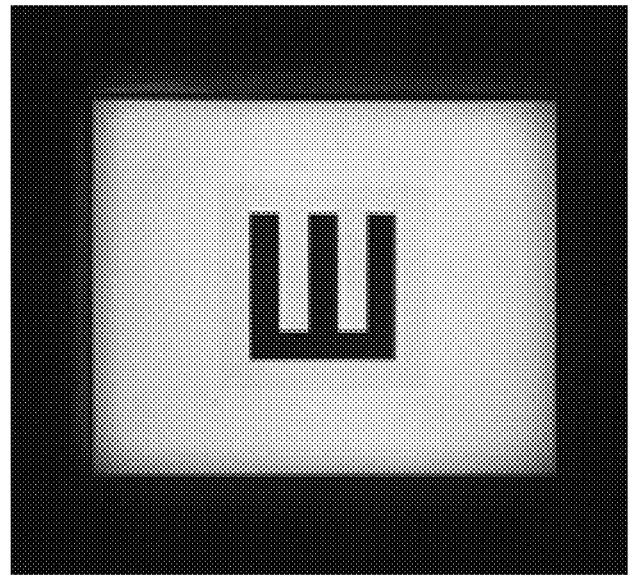
FIG. 19 depicts a sharp image by use of a disclosed embodiment

FIG. 19 depicts a more clear view derived by use of a disclosed embodiment.

In a disclosed embodiment, a first lens 320 has a front surface 325 comprising of an aspherical surface, with the aspherical surface used to reduce the optical distortion, such as the barrel effect, observed by a subject using a disclosed embodiment 100. Optical distortion may be considered an optical aberration that deforms and/or bends sight lines, resulting in a curvy or blurred image as exemplified in FIG. 18. The image of FIG. 18 was obtained by use of lenses with spherical surfaces wherein barrel distortion is especially visible along the four outer edges of the image. The four outer straight edges appear to curve as if compressed within a barrel. This phenomenon is sometimes referred to as "barrel distortion." The disclosed embodiments overcome the barrel distortion of the prior art by use of the disclosed lens system 300 wherein superior results are obtained, as exemplified in FIG. 19.

By use of the disclosed embodiments, shortfalls in the prior art are overcome, such as the short fall of barrel distortion and the short fall of requiring a 20 foot distance between the test subject and the eye chart. The superior results of the disclosed embodiments, as shown in FIG. 19 include significantly reduced barrel distortion wherein the four outside edges appear to be straight or nearly straight.

In the prior art, conventional lenses are made with spherical surfaces. Spherical lenses are known to introduce optical aberrations, such as barrel distortion. A single surface of aspherical profile can greatly reduce the aberration, compared to using a complex spherical lens group. In some of the presently disclosed embodiments, the first surface 325 of the first lens 320 is made with an aspherical profile, meaning that the radius of curvature is not constant across the diameter. A material function of the aspherical surface is to reduce optical distortion and to reproduce the same clear image as viewed from a prior art eye chart at a distance of 20 feet. The second surface 330 of the first lens 320 has a concave spherical profile. The first lens 320 provides a demagnified optical power to generate a virtual image that is approximately three times smaller than the image displayed upon the screen of a smartphone.

The second lens 360 may comprise a spherical convex lens. The second lens 360 creates yet another virtual image or optical image from the first virtual image or optical image created by the first lens 320, at a distance of 20 feet away from the eye. The second lens 360 may have a magnifying optical power of approximately 100.

Overall, a disclosed optical system may have a magnification of around 30. Thus, the letter size displayed upon and by the attached smartphone is about 30 times smaller compared to the letter size of a prior art paper eye chart used for a 20 foot vision test.

Figure 20:
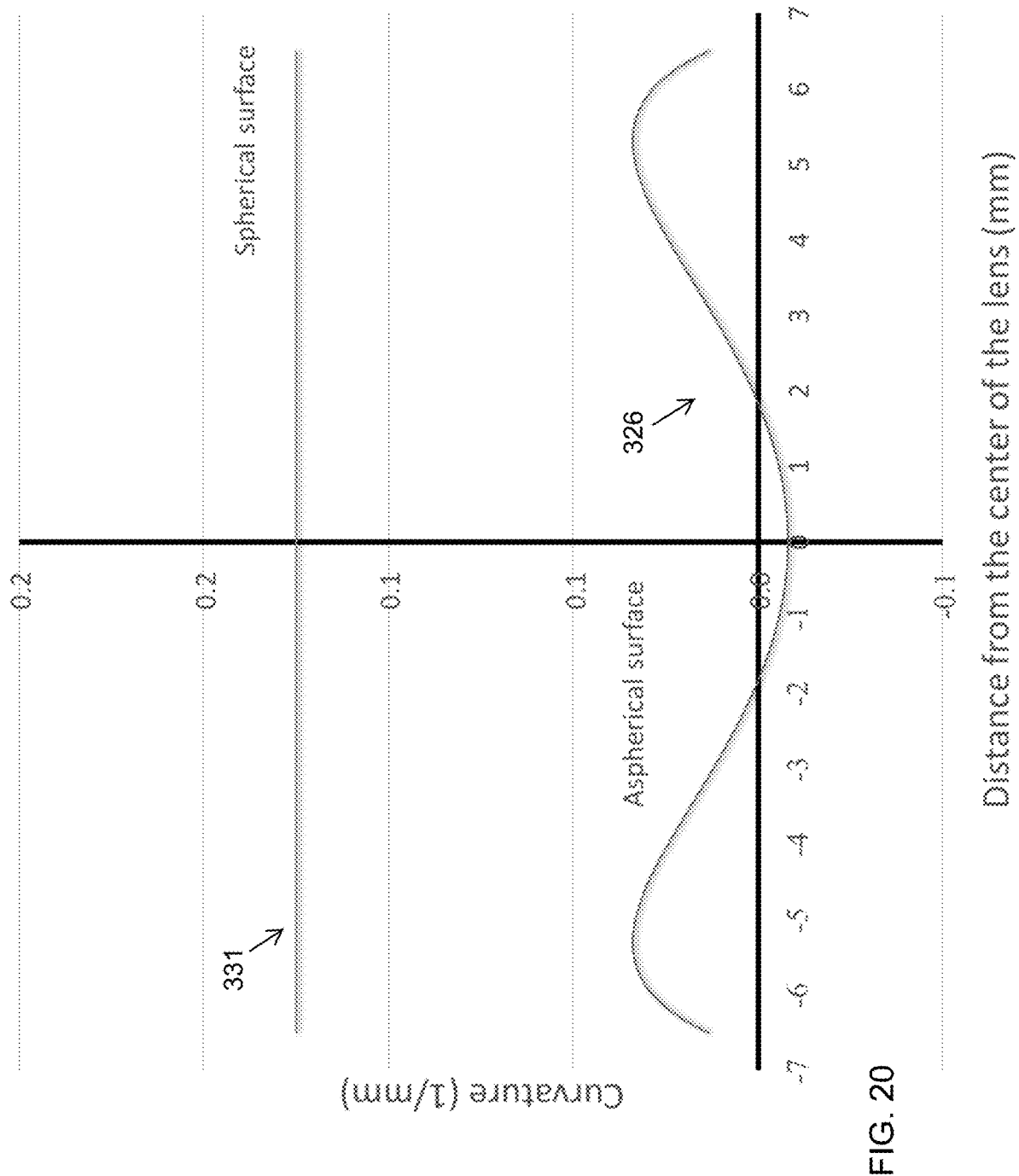
FIG. 20 depicts a graph of lens surface properties

FIG. 20 discloses the best mode known to date for implementing the aspherical surface 325 of the first lens 320. The curved line 326 depicts the curvature value of the aspherical surface, the first surface 325. The straight horizontal line 331 depicts the curvature value of the spherical surface, or second surface 330 of the first lens. The horizontal x axis measures distance in millimeters from the center of a lens while the vertical y axis measures lens curvature in millimeters.

FIG. 21A depicts a front view of a first lens. The first lens may have an outer diameter of 14 mm and an inner diameter of 12 mm.

FIG. 21B depicts a cross sectional view of FIG. 21A. FIG. 21B shows the aspherical surface 325 of the first lens and also shows the concave back surface 330 of the first lens. The outer distance may be 4.71 mm with an inner distance of 2 mm.

FIG. 21C depicts a perspective view of the first lens.

FIG. 22A depicts a front view of a second lens 360 which may have an outside diameter of 12 mm and inside diameter of 11 mm.

FIG. 22B depicts a side view of a second lens wherein the second lens may have a width of 2.8 mm.

FIG. 22C depicts a perspective view of a second lens 360.

Figure 23:
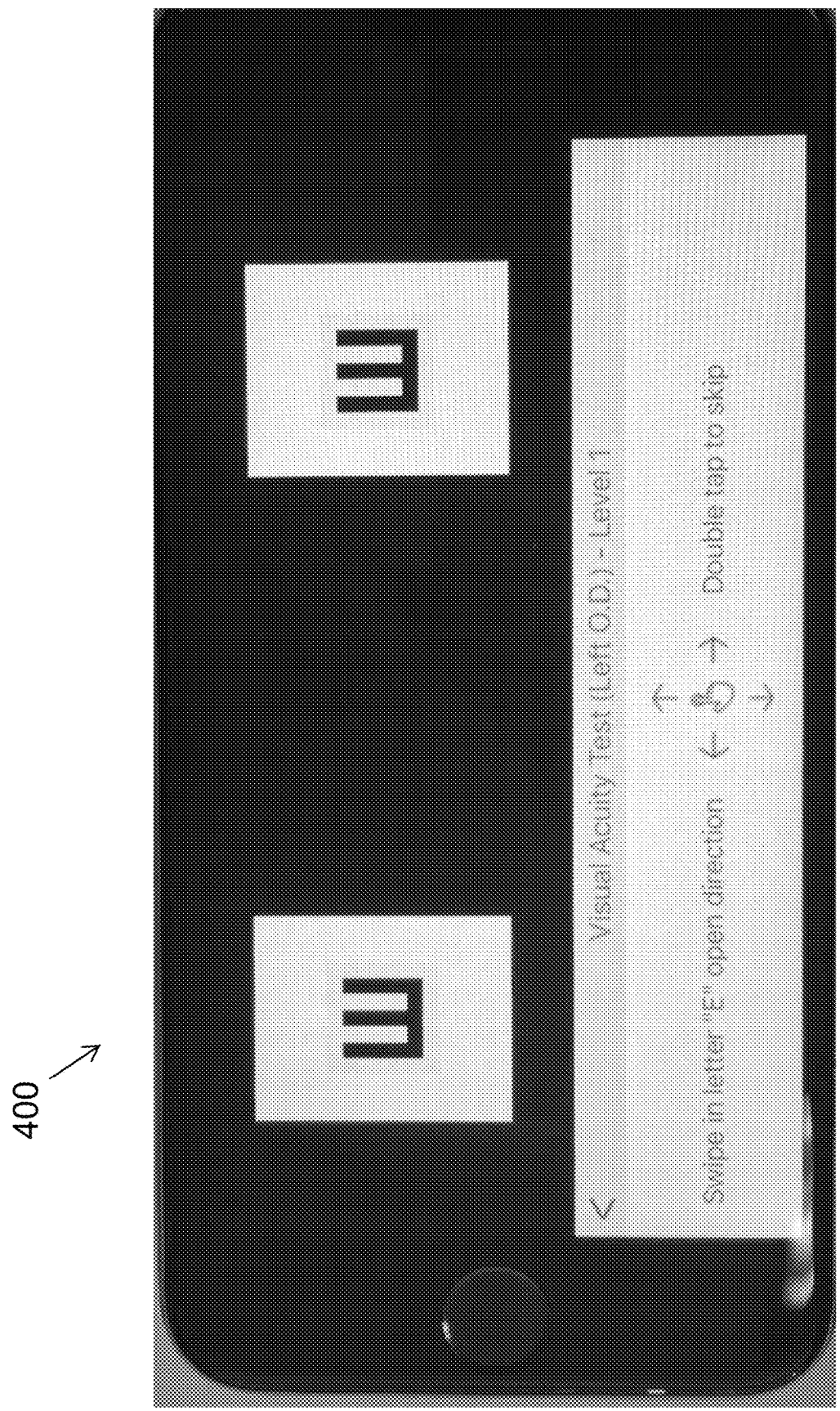
FIG. 23 depicts an eye chart image generated upon a smart phone screen

FIG. 23 depicts an image such as an "E" displayed upon a smart phone screen.

Figure 24:
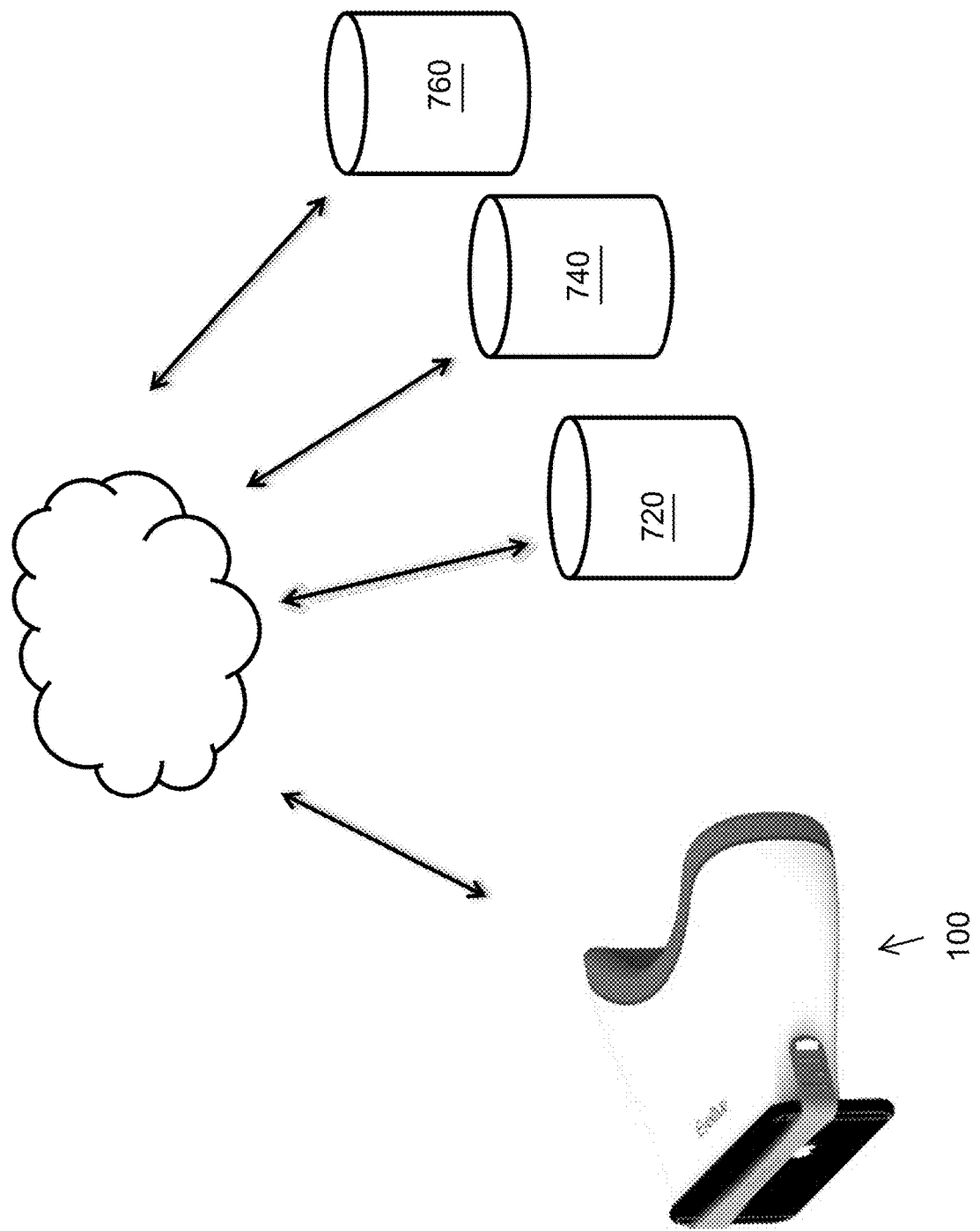
FIG. 24 depicts a flow chart of information obtained from a disclosed embodiment

FIG. 24 depicts a flow chart of information flowing from a disclosed embodiment 100 to a cloud storage 700 or communication system with the collected data stored or used by a plurality of database systems or outside systems that may include a user measurement database 720, an eye care professional database 740 and a eyeglass production facility database 740.

Figure 25:
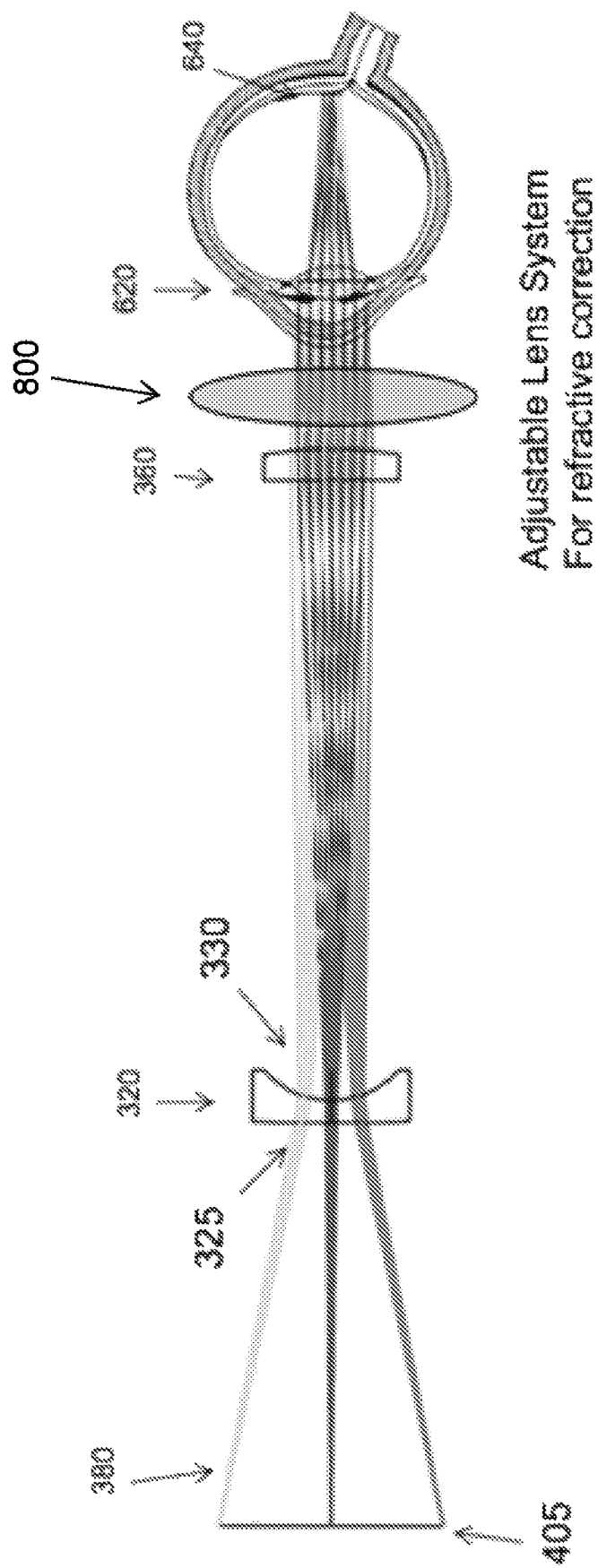
FIG. 25 depicts an adjustable lens system for refractive correction and other components

FIG. 25 depicts lenses and sightlines with the addition of an adjustable lens system 800 for refractive corrections and other functions.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

All the above references and U.S. patents and applications are incorporated herein by reference. Aspects of the invention can be modified, if necessary, to employ the systems, functions and concepts of the various patents and applications described above to provide yet further embodiments of the invention.

These and other changes can be made to the invention in light of the above detailed description. In general, the terms used in the following claims, should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

While certain aspects of the invention are presented below in certain claim forms, the inventors contemplate the various aspects of the invention in any number of claim forms.

What is claimed is:

1. A method for adjusting sight lines from an image produced by screen such that the adjusted sightlines replicate the sightlines perceived by an optical system viewing a physical eye chart, the method comprising the steps of:
   a) using a first lens in visual communication with an image presented upon a display screen, wherein the first lens demagnifies the image presented upon the screen; wherein the first lens uses an aspherical surface that is proximal to the display screen and wherein the first lens uses a concave surface that is distal to the display screen;
   b) using a second lens in visual communication with the first lens, wherein the second lens magnifies the demagnified image sent by the first lens;
   c) presenting the magnified image from the second lens to an end user; and
   d) using a deformable adjustable lens system to form a phoropter device, allowing estimates of the user's refractive error in each eye, the deformable adjustable lens system disposed between a user's eye and the second lens.

2. The method of claim 1, further including the step of using an aperture piece to constrict the image presented upon the display screen as perceived by the first lens.

3. The method of claim 2, further including the step of using a pair of lens tubes to keep a first set of first and second lenses and a second set of first and second lenses in alignment.

4. The method of claim 3, further including the step of moving the pair of lens tubes to comport with the PD of an end user.

* * * * *